United States Patent [19]

Kiser et al.

[11] Patent Number: 5,418,142
[45] Date of Patent: * May 23, 1995

[54] GLUCOSE TEST STRIP FOR WHOLE BLOOD

[75] Inventors: Ernest J. Kiser, Los Altos; Edward G. Rice, Palo Alto; Michael F. Tomasco, Mountain View, all of Calif.

[73] Assignee: Lifescan, Inc., Mountain View, Calif.

[ * ] Notice: The portion of the term of this patent subsequent to Apr. 26, 2011 has been disclaimed.

[21] Appl. No.: 960,579

[22] Filed: Oct. 13, 1992

Related U.S. Application Data

[63] Continuation of Ser. No. 691,192, Apr. 25, 1991, abandoned, which is a continuation of Ser. No. 399,055, Aug. 28, 1989, abandoned.

[51] Int. Cl.$^6$ ............ C12Q 1/54; C12Q 1/00; G01N 21/00
[52] U.S. Cl. .................................. 435/14; 435/4; 435/25; 435/28; 422/56; 422/57; 422/101
[58] Field of Search ............ 435/4, 14, 25, 28; 422/56, 57, 101; 436/177, 95

[56] References Cited

U.S. PATENT DOCUMENTS

| | | | |
|---|---|---|---|
| 3,992,158 | 11/1976 | Przybylowicz | 23/253 |
| 3,995,019 | 11/1976 | Jerome | 424/1.5 |
| 4,018,883 | 4/1977 | Parslow | 424/1 |
| 4,734,360 | 3/1988 | Phillips | 435/25 |
| 4,824,639 | 4/1989 | Hildenbrand | 422/56 |
| 4,828,710 | 5/1989 | Itoh | 210/675 |
| 4,994,238 | 2/1991 | Daffern | 422/56 |

*Primary Examiner*—Jeffrey E. Russel
*Assistant Examiner*—Ralph Gitomer

[57] ABSTRACT

A separation matrix impregnated with a separating agent separates red blood cells or hemoglobin from whole blood. Upon separation, an impregnated test reagent reacts with the separated substantially clear component fluid to form a colored product which enables a visual or meter test for glucose levels in whole blood.

18 Claims, 2 Drawing Sheets

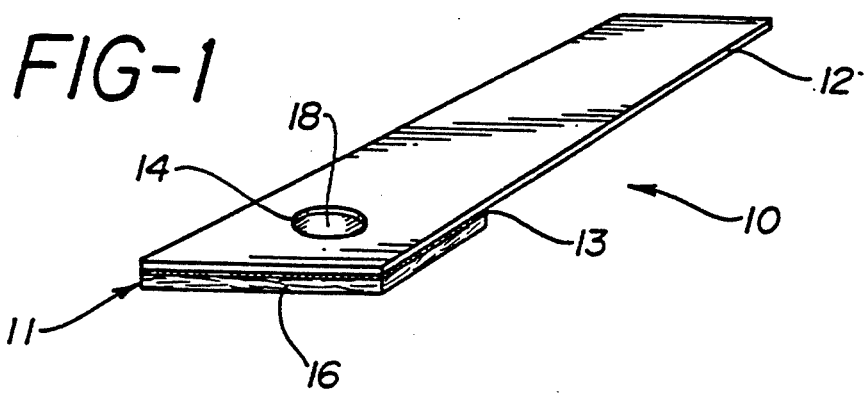
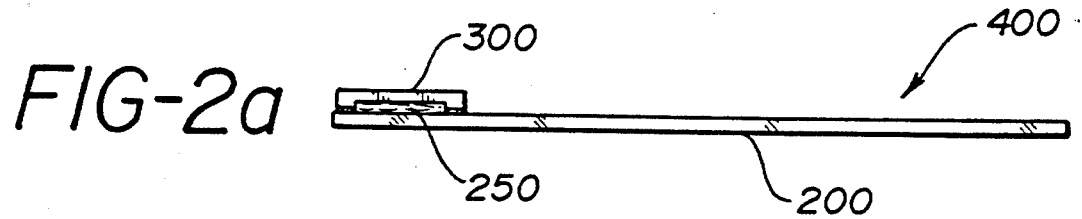
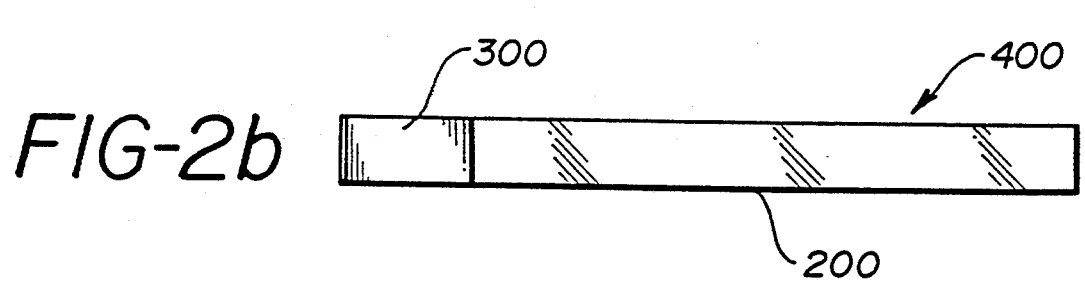
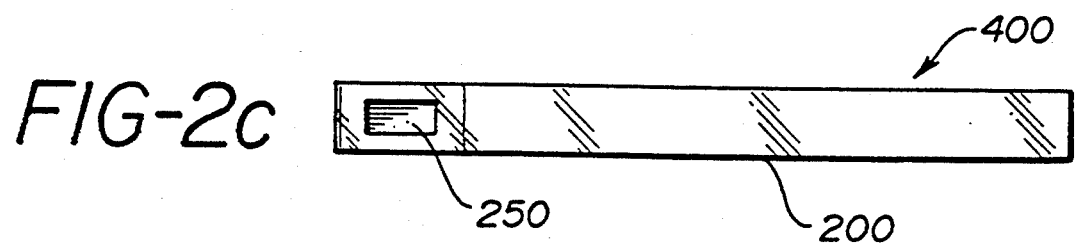

GLUCOSE TEST STRIP FOR WHOLE BLOOD

This is a continuation of application Ser. No. 07/691,192, filed Apr. 25, 1991, now abandoned which is a continuation of application Ser. No. 399,055, filed Aug. 28, 1989, now abandoned.

FIELD OF THE INVENTION

The present invention relates to a technique which allows the user to comparatively determine analyte levels in whole blood. More particularly, the present invention relates to a comparative reagent strip which allows the user to determine levels of analytes in whole blood. Most specifically, the present invention relates to a comparative reagent strip which separates whole blood into cells and a fluid and from which is determined analyte levels through means of a visual test or various instrumental means.

BACKGROUND OF THE INVENTION

Numerous simple visual test devices have been developed for the analysis of body fluids in order to determine component analyte amounts. These tests include such devices as means for detecting glucose or other sugars in urine or in blood as well as protein in urine, ketones, uric acid, phenylalanine or enzymes, only to mention a few. All of these tests detect various soluble analytes.

Yet, it has been particularly difficult to perform visual tests of these constituents in whole blood. This difficulty lies in the problems associated with visual responses to the presence of red blood cells in whole blood. The dense red coloration of red blood cells and hemoglobin seriously interferes with such analysis.

Means have been proposed for separating and removing highly colored red cell components from whole blood prior to analysis. Some of the simpler methods involve the use of a carrier member impregnated with a test reagent composition and coated with a semipermeable membrane which effectively acts as a means for screening out large molecules such as hemoglobin. This semipermeable membrane permits the passage of smaller molecules or ions in the solution. A substantially clear fluid containing the constituent diffuses into the test reagent in the carrier to cause a chromogenic reaction with the reagent.

Other methods provide for the drawing of whole blood, then allowing the blood to clot. Once clotted, the blood is centrifuged to separate cell components.

These methods are cumbersome and generally laborious and require at least one extra manipulative step such as wiping, blotting or rinsing with water. This amounts to considerable loss in time and more importantly, accuracy and efficiency. Moreover, the membrane screens out larger molecules in solution, which precludes these molecules from reaching the test reagent. This sometimes renders these methods inoperative for particularly needed determinations. These methods are also technique-dependent and difficult for untrained operators to perform.

Other methods have included taking whole blood samples and placing such samples on a bicomponent reagent strip. After a predetermined time period lapses, the blood sample is blotted to remove excess blood. At that point, constituents of the whole blood sample react with molecules in the reagent strip, and a visual comparison test is performed.

Other test systems may comprise a single matrix which contains both a separating reagent and a test reagent in such a way that the whole blood first contacts the separating reagent to form a substantially colorless fluid which then contacts the test reagent. In employing such a single matrix test system the separating reagent must be compatible with the test reagent for both reaction and stability during storage. The matrix must be designed so that the blood sample reaches the area of the device where the response is read substantially free of any blood coloration. In such an embodiment, a porous support is first coated or impregnated with the test reagent and subsequently the surface of the matrix is coated or impregnated with the separating reagent. In such a test device, the whole blood is contacted with the separating reagent and the test response is observed in an area not initially contacted with the blood and to which the substantially colorless fluid or serum has migrated.

Examples of such single matrix test strips included separating reagents which have been found to be, among other things, water-soluble salts, amino acids and carbohydrates such as mannitol. Some of these chemicals cause hemolysis which releases cellular constituents, including hemoglobin. The salts found effective as separating reagents are non-volatile and do not decompose to any extent under the conditions of preparing and utilizing the test device. The salts have been defined as having solubility in distilled water of at least about 1 gram per liter at 20° C.

In many instances, red blood cells or hemoglobin continue to seep through the separating reagent so that the test reagent encounters colored blood components. When this occurs, accuracy levels are destroyed, and visual comparison is difficult.

It is thus an object of the present invention to provide a unitary test device, wherein during one step the user can apply an unmeasured sample of whole blood and determine analyte levels in the whole blood sample.

It is therefore another object of the present invention to provide a unitary test device wherein the test device, whether single or multi-layer, contains separating means as well as test reagent.

It is a further object of the present invention to form a test device consisting of a single matrix wherein whole blood samples can be applied to one side and visual comparisons of analyte levels can be made at the opposite side of the test strip, or alternatively in a longitudinal transport device, such readings made on a second portion of test strip after wicking.

It is yet a further object of the present invention to determine glucose levels in whole blood samples where a wholly unmeasured sample of whole blood is applied to a single side of a reagent strip. The separating reagent and test reagent are coated on or trapped within the reagent strip and both work effectively and simultaneously to separate and react with the separated clear fluid sample in order to determine, visually, glucose levels of the wholly unmeasured whole blood sample.

It is finally an object of the present invention to provide a test device such that whole blood is analyzed in a single manipulative step for selected molecular constituents such as glucose by a combination of separation means and detection means.

SUMMARY OF THE INVENTION

These and other objects of the present invention are accomplished in a single membrane test strip which is attached to a support member. This test strip is treated with both a separating reagent and a test reagent. Both the separating reagent and test reagent may be found throughout the entire test strip matrix or may be found predominately on one side of the matrix. In the method of the present invention, whole blood is applied to one side of the matrix. As the whole blood passes through the matrix, separation and reaction occur. Ultimately, the whole blood is separated into red blood cells and a substantially colorless fluid. Because the matrix is configured with such a thickness to cause the red blood cells to become separated within a first portion of the strip of the matrix, the lower portion of the matrix containing a substantially colorless constituent reacts with the test reagent alone. The test reagent is, of course, configured to accurately determine (visually) the predetermined levels of analytes. Therefore, the resulting configuration on the test side of the matrix will be a test reagent which has reacted to the clear constituent and enables visual or instrumental determination of analyte levels.

In an alternate embodiment of the present invention, whole blood is placed on a testing surface comprising a disc of porous material, which is then contacted with a matrix treated with both separating reagent and test reagent. This closed strip then allows the blood to separate and react in the same fashion. A final visual comparison is then made on the test side of the matrix.

In addition, the present invention may be configured so that a separating membrane and reagent membrane are incorporated within the same test strip. The same separation techniques are applied to the whole blood sample. After separation, the same reaction takes place between the separated sample and the reagents in a reagent membrane. Alternately, the device may be configured so that varying degrees of separation or reaction may take place simultaneously in the matrix on the same layer. Therefore, visual comparison can be made on the test side of the reagent matrix.

The present invention will be more accurately understood in conjunction with the following detailed description of the invention as well as the present detailed description of the drawings.

BRIEF DESCRIPTION OF THE DRAWINGS

FIG. 1 is a perspective view of a preferred embodiment test strip of the present invention illustrating a matrix fastened to a plastic holder which defines a hole;

FIGS. 2a, 2b and 2c are top, bottom and side views respectively of an alternate preferred embodiment of the present invention, respectively, depicting a plastic support upon which are fastened two separate matrices;

DETAILED DESCRIPTION OF THE INVENTION

Figure 3:
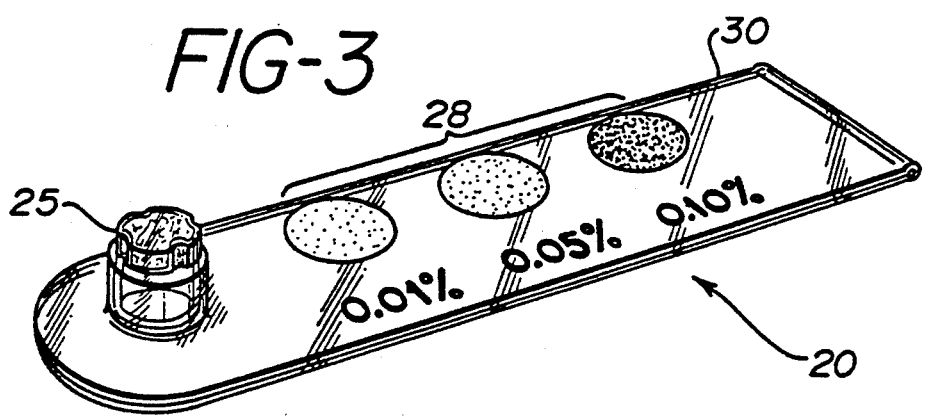
FIG. 3 is a perspective view of a second alternate preferred embodiment of a test strip of the present invention in a closed position showing a clear support which defines a well.

The subject invention provides an improved rapid, simple methodology implying reliable and easy to operate apparatus for determination of analytes such as glucose, particularly involving a substrate which results in the change in color in order to determine analyte levels in whole blood. The method involves applying to a porous matrix a small volume of whole blood, sufficient to saturate the matrix. The matrix may be either one single layer or a combination separation matrix and reagent matrix. Bound to or contained in the matrix are one or more reagents of a signal producing system, which results in production of a change in the color of the matrix when combined with analytes in blood. The liquid sample penetrates the matrix and an observation is made on the opposite side of the matrix from where the sample is placed, as a result of the separation of whole blood into clear and colored constituent components and reaction of the clear component with a testing reagent.

For measurements of blood, particularly glucose measurements, whole blood is typically used as the assay sample. The matrix will contain both a separating agent and a reaction agent. The reaction agent produces a light absorbing product which changes either color or intensity dependent upon concentration of the analyte in the whole blood sample. The time span within which the blood is able to be separated and reacted typically varies from about 15 seconds to about 5 minutes.

The first component of the present invention comprising the reagent test strip 10 to be considered is a reagent element 11, as seen in FIG. 1. This reagent element 11 comprises an inert porous matrix 16 and the component or components of a signal producing system, which is capable of reaction with an analyte to produce a color variable reaction product on the non-sampling side of the porous matrix 16. As previously noted, the porous matrix 16 may be a single or multilayer element. The signal producing system allows flow of liquid through the matrix. In order to assist in reading the color-produced scheme, it is preferred that the matrix 16 have at least one test side 18 which is substantially smooth and flat. Typically the matrix will be formed into a thin sheet with at least one smooth, flat side.

In use, the liquid sample being analyzed is applied to one side of the matrix 16 sheet whereby the desired analyte passes through the reagent element by means of capillary action, wicking, gravity flow and/or diffusion. The components of the signal producing system present in the matrix will react to give a light absorbing reaction product, whose color will be dependent upon the analyte concentration in the liquid sample.

The first component of the reagent element 11 is the matrix 16. The matrix will be a matrix to which reagents may be covalently or noncovalently bound or impregnated. The matrix 16 will allow for the flow of an aqueous medium through the matrix 16. The matrix 16 will also retard passage of whole blood cells through the matrix without substantial hemolysis and without significantly adversely affecting the identity or concentration of the analyte in the blood sample. Composition of the matrix 16 will be of sufficient thickness, preferably 50 to 3000 microns, to permit the formation of a colored reaction product on the test side 18 of the matrix, opposite a side where the sample is applied, so that essentially clear constituent reacts with the test reagent embedded in the matrix 16. The matrix 16 also should not deform substantially upon wetting so as not to interfere with subsequent quantitation. The matrix 16 thus substantially retains its original size and flatness.

As exemplary of matrix surfaces are porous polyethylenes, especially matrices having a porosity of between 0.5 and 150 microns. Especially useful are matrices which are coated with polyethylene glycol, polystyrene sulfonic acid or polyvinyl sulfonic acid at a pH between 4.0 and 8.0. However, it has been observed that sufficiently opaque thicknesses of paper will also be effective as a matrix, as well as woven or non-woven polyesters and polyamides and other absorptive surfaces, such as nitrocellulose.

Most particularly however, it has been found that a composite polyester membrane is most effective when treated with reagents such as polyethylene glycol. Yet, also effective is the porous polyamide reagent membrane used in the One-Touch TM device made by the present assignee.

One manner of preparing the porous material is to cast the polymer onto a core of nonwoven fibers. The core fibers can be any fibrous material with requisite integrity and strength, such as the aforementioned polyesters or polyamides. The reagent that will form the separating and reacting material is present within the pores of the matrix 16 but does not block liquid flow through the matrix 16. Thus, the separated clear constituent can pass through the pores of the matrix 16, while red blood cells and hemoglobin are retarded at or near the matrix surface.

A matrix of less than about 3000 microns thickness is usually employed with about 100 microns to about 1000 microns being preferred. Typically, the matrix 16 will be attached to a holder in order to give it physical form and rigidity, although this is not essential. FIG. 1 shows an embodiment of the invention in which a thin reagent element comprising reagent element 11 is positioned at one end of a plastic holder 12 by means of an adhesive 13 which directly and firmly attaches the reagent pad. A hole 14 is present in the plastic holder 12 in the area to which reagent element 11 is attached so that sample can be applied to one side of the reagent element 11 and reaction product observed on the opposite side 18.

A liquid sample to be tested is applied to reagent element 11. Generally, with blood being exemplary of a sample being tested, the matrix 16 will be on the order of about 10 mm sq. to about 100 mm sq. in surface area, especially 10 mm sq. to 50 mm sq. in area, which normally a volume of 5 to 20 microliters of sample will more than saturate. As can be seen in FIG. 1, the plastic holder or support 12 holds reagent element 11 so that the sample can be applied to one side of the reagent element 11 while color can be observed on the opposite side of the reagent element 11.

Figure 4:
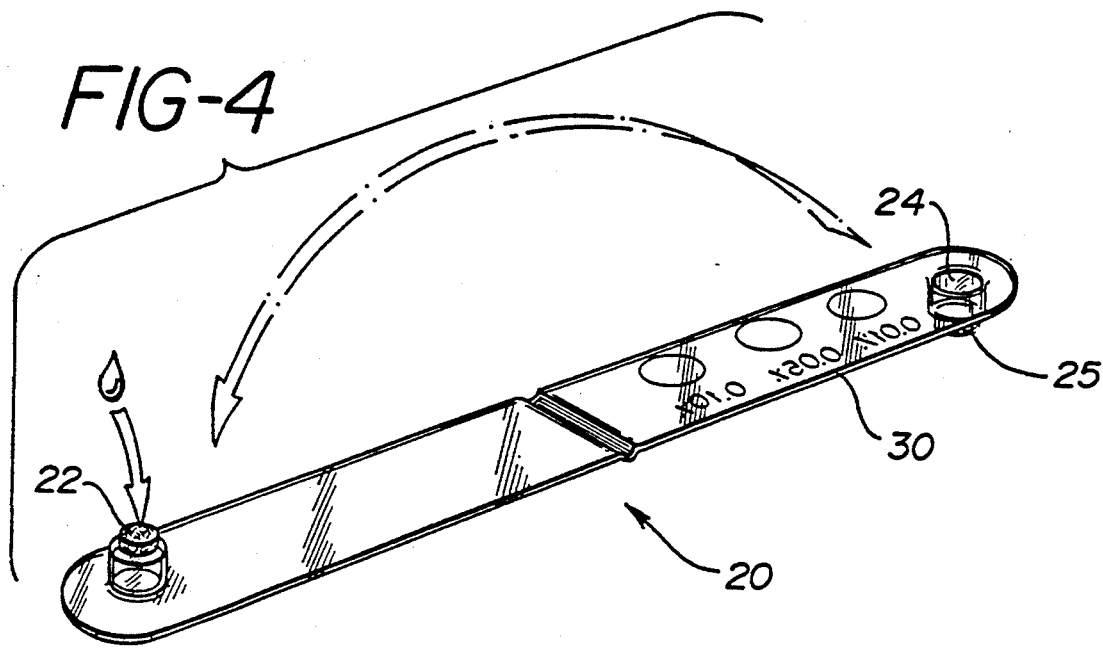
FIG. 4 is a perspective view of a second alternate embodiment of the present invention in an open position.
Figure 5:
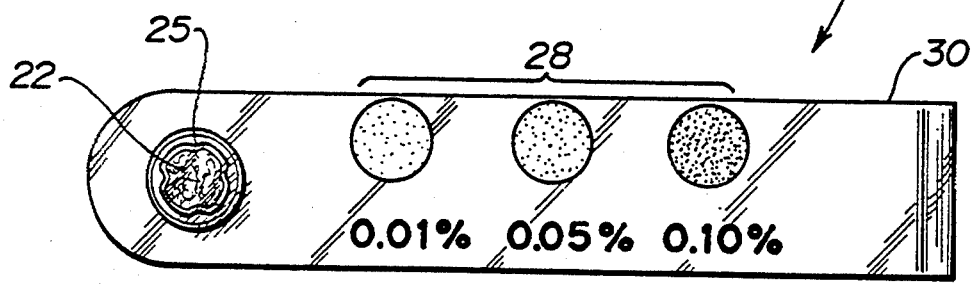
FIG. 5 is a top view of the second alternate preferred embodiment of the present invention in the closed position, which displays the manner in which the support may be folded.

FIGS. 3, 4 and 5 show a system in which reagent is applied to a porous disc 22 on one side of a folding reagent test strip 20. This folding strip contains a reagent matrix well 24 opposite disc 22 which fits into well 24 when strip 20 is folded. As seen in FIGS. 3 and 4, the strip 20 is folded so that the reagent matrix 25 can react with a whole blood sample. As seen in FIG. 5, what is observed will be the reaction product which can be colorimetrically compared to typical colors formed by reaction product placed on scale 28 alongside the pad.

The matrix 11, embodied in FIG. 1, and matrix 24 embodied in FIGS. 3, 4 and 5 may be attached to the plastic holder 12, embodied in FIG. 1, and the; after "support", delete support "30" and insert therefor 20, embodied in FIGS. 3, 4 and 5, by any convenient means, e.g. a holder, clamp or adhesives; however, the preferred method is bonding. The bonding can be done with any nonreactive adhesive, by a thermal method in which the backing surface is melted enough to entrap some of the material used for the matrix, or by microwave or ultrasonic bonding methods which likewise fuse the matrix to the backing. It is important that the bonding be such as to not itself interfere substantially with the reaction between reagent element and whole blood sample as well as the separation process in the matrix. For example, referring now to FIG. 1, adhesive 13 can be applied to the backing of plastic roller 12, followed first by punching hole 14 into the combined plastic holder and reagent element 11 and then applying matrix 11 to the adhesive 13 in the vicinity of hole 14 so that the peripheral portion of the reagent pad element 11 attaches to plastic holder 12.

Among other things, the separating agent should be capable of producing a relatively clear colorless fluid by removing the red cells from whole blood. Separating reagents must be contained within the matrix in cooperation with reaction reagents, which will later be explained. In varying degrees, water soluble salts effect such separation. Among salts operable as separating reagents in the present test device are citrates, formates and sulfates as well as certain acids such as amino acids, citric acid, phytic acid and malic acid.

In addition to such salts or acids, polymeric separating agents have also been effective, such as polyethylene glycol, polystyrene sulfonic acid, polyvinyl sulfonic acid and polyvinyl alcohol in conjunction with membranes such as the Pall BioSupport TM membrane. It is necessary to treat a portion of the matrix with such a separating agent.

Signal producing systems typically employed in light reflectance measurements can also be used for colorimetric readings. As previously described, the separating reagents cause whole blood to be separated from red blood cells producing a substantially clear constituent. At that point, signal producing systems such as those embodied in the previously referenced One-Touch TM test strip may be employed with the analyte in the sample to produce compounds characteristically visually observable on the opposite side of the matrix bound to the reagent strip. Alternately, the strip may be optically tested in conjunction with a meter, such as that employed using the previously referenced One-Touch TM system.

The preferred analysis method is to apply an unmeasured drop of whole blood on one side of the reagent pad. As the whole blood sample moves across the reagent pad it reacts with the separating agent to become separated from red blood cells. At that point, a substantially clear colorless component is separated from the red blood cells and the analyte in the component reacts with the embedded reacting agent in order to produce a colorimetric change.

In an additional preferred embodiment as seen in FIGS. 2a, 2b and 2c, there is made available a reagent test strip 400 comprising plastic support 200, which is adhesively connected to a coated-reaction matrix 250 and a coated separation matrix 300. Each of these components of the test strip 400 will be explained in sequence.

The first component is the coated separation matrix 300. This separation matrix will generally be between 50 and 3000 microns in thickness. The matrix is formed from among the families of polyesters, polyamides, polyolefins or cellulosics. Among the available materials useable to coat the separation matrix 300 are polyvinyl sulfonic acid, (PVS 19), polyethylene glycol (PEG), polystyrene sulfonic acid (PSSA), hydroxypropyl cellulose (commercially available as Klucel TM ), polyvinyl alcohol (PVA), polyvinylpyrrolidone (PVP), polyacrylic acid (PAA) or any such materials with particulate additives such as silica or clay including a type of clay commonly identified as bentonite.

This separation matrix layer 300 is combined with a reagent coated reaction matrix 250 placed below or within the separation matrix 300. The reagent matrix 250 may be chosen from among polyamides, polyesters, polyolefins or cellulosics. Reaction matrix 250 is embedded with solution. All indicator solutions described are provided in a 0.1M, pH 5.0 citrate buffer containing 1% Klucel TM -EF with glucose oxidase at 6 mg/ml and horseradish peroxidase at 2 mg/ml. The indicator solutions useful as reagents for coating the reaction matrix 300 may be chosen from among (a) 3-methyl-2-benzothiazolinone hydrazone hydrochloride (MBTH) combined with 3,3-dimethylaminobenzoic acid (DMAB); (b) MBTH combined with 3,5-dichloro-2-hydroxybenzenesulfonic acid (DCHBS); (c) 4-aminoantipyrene(4-AAP) (at 4mg/ml) and 5-oxo-1-(p-sulfophenyl)-2-pyrazoline-3-carboxylic acid (OPSP); (d) 4-AAP (at 4mg/ml) and N-(m-tolyl)-diethanolamine (NDA); (e) $2,2^1$-azino-di(3-ethylbenzthiazoline) sulfonic acid (ABTS); or (f) 4AAP (at 4 mg/ml) and 4-methoxynaphthol.

Further regarding the indicator solutions described above, the MBTH concentrations are found most effective at 2 mg/ml. In addition, when MBTH is combined with DMAB or DCHBS, each of these other components are used within the matrix at concentrations of 2 mg/ml. The 4-AAP/OPSP concentration is generally used 1 mg/ml. On the other hand, NDA concentrations can be used most effectively at 0.2 mg per ml. As well, the ABTS combination is most useful at 5 mg per ml. In addition, these reagents can be combined with substances such as polyethylene glycol or Klucel TM in order to be better bound to the reaction matrix 250.

It has been found that the polymer coated separation matrix 300 may use a reagent as a surface tension modifier or analyte releaser and then be combined with a reagent coated reaction matrix 250. In fact, it has been found that tetraethyleneglycol dimethyl ether is quite useful in performance of the present invention.

In addition, the separation matrix 300 has been found effective when a reagent component is coated within the separation matrix 300 itself. Of course, additional reagent components are then used within the reaction matrix 250 of the same test strip 400. It has been found quite useful to use a separation matrix 300 comprised of polyethylene with a polyethylene glycol separation coating and including within the separation matrix 300 a glucose oxidase and an appropriate citrate buffer. As well, in the reaction matrix 250 it is useful to provide any of the listed indicator solutions combined with a coating of horseradish peroxidase and the MBTH-DMAB combination.

Certain separation matrix 300 coatings have been found quite useful to adequately separate whole blood samples. Any of the above matrix materials can be used wherein the separation matrix coatings and solvents and combinations are chosen from the following:

1. 35% weight per volume (W/V) PEG 3500 in methylene chloride on fine polyethylene
2. 10% (W/V) PVSA and 1% (W/W) Bentonite in water at pH 5.0 fine polyethylene
3 13% (W/V) Monostearate of PEG in methylene chloride on fine polyethylene
4. 20% (W/V) PEG 1000 and 2% (W/W) Bentonite in methylene chloride on nonwoven rayon
5 4% (W/V) Tetraethyleglycol dimethyl ether and 30% (W/V) PEG 1000 in methylene chloride on nonwoven polyester
6. 15% (W/V) PVSA and 0.2% (W/V) PVA 10000 in water at pH 4.5 on a polyethylene or a woven nylon membrane
7. 7% (W/V) PVSA in water at pH 4.5 on Pall L/4 polyester Finally, the preferred reagent matrixes 250 have been found to be useful:

1. "One Touch" ® reagent membrane,
2. MBTH plus DCHBS on a polyamide membrane,
3. 4-AAP plus NDA on a polyamide membrane Finally, it should be noted that the plastic support 200 should be between 50–1000 microns in thickness and be comprised of a transparent, clear plastic. This plastic support provides support for the entire mechanism, and provides the base for the testing apparatus.

Thus, the separation matrix 300 is placed above the reaction matrix 250 and is adhered to the clear plastic support 200. When a whole blood sample is placed upon the separation matrix 300 layer, the blood sample is separated in the separation matrix 300 and then enters the reaction matrix 250. In the reaction matrix 250, the separated blood reacts with the reagent, which is coated in the reaction matrix 250, and a color change is visible through the clear plastic support 200. At the surface of the clear plastic support 200 a comparison can be made with a standardized color chart to determine levels of analyte, in this particular case, glucose.

Generally, in all the preferred embodiments it is preferred for the color to vary in intensity or hue dependent on analyte concentration. It has been found that the particular configurations of reagents is particularly suited to vary intensity of reaction product color from a light to a dark color with glucose measurements.

Of course, two factors must be present. First, the reagent test strip must have a matrix or matrices of the above specified thicknesses in order to appropriately separate the blood and create a large enough barrier to maintain the originally clear surface on the opposite side of the matrix. Second, the varying color change must suitably reflect analyte level concentrations to the human eye or any other measuring device.

It is well recognized that once the separating agent has separated the red blood cells or hemoglobin from the substantially clear colorless constituent, one is capable of performing any desired test for analyte present in such separated constituent. Specifically, with appropriate reagents, one can measure cholesterol or alcohol levels in whole blood. Such is an intended use of the present device in conjunction with the appropriate known reagents embedded within the matrix.

It is therefore intended that the previous examples not limit the scope of the present invention which is to be determined from the following claims and their equivalents.

What is claimed is:

1. A reagent test strip comprising:
    a porous matrix having an internal surface which defines pores and upon which a separating coating and a test reagent are disposed;
    an elongated support having two opposite ends said matrix overlying and affixed to at least a portion of said support at one end of said support; and a porous disc overlying and affixed to said support at the opposing end of said support;

said matrix is capable of passing a sample of whole blood;

wherein said separating coating is capable of separating from said whole blood a substantially clear component fluid containing glucose;

said test reagent is capable of reacting with said analyte in said substantially clear component fluid to vary coloration of said matrix dependent upon the level of said analyte in said whole blood sample; and the porous disc is secured to one end of said support and the matrix is secured to the opposing end of the support such that an unmeasured blood sample may be placed on said porous disc and thereafter the support can be manipulated to bring a portion of the porous disc into contact with the matrix, and the side of the matrix facing away from said porous disc can be visualized.

2. A reagent test strip comprising:

a porous matrix of a material selected from the group consisting of polyesters, polyamides, polyolefins, and polysulfones, having a sample side and a test side and defining an internal surface, said matrix having disposed upon said internal surface throughout said matrix, both a separation coating and a testing reagent;

wherein said matrix, when applied on said test side with a sample of whole blood suspected of containing glucose is capable of accepting said whole blood sample so as to pass it toward said test side;

said separation coating is capable of separating from said whole blood a substantially clear component fluid containing said glucose;

said testing reagent is present in an amount effective for reacting with said glucose in said clear component fluid to vary coloration of the test side of said matrix, dependent upon the concentration level of the glucose in said fluid; and said separation coating and said testing reagent being compatible with each other whereby said separating and reacting may occur simultaneously.

3. The reagent test strip of claim 2 wherein said testing reagent is:

3-methyl-2-benzothiazolinone hydrazone hydrochloride with 3,3-dimethylaminobenzoic acid.

4. The reagents test strip of claim 2 wherein said testing reagent is:

3-methyl-2-benzothiazolinone hydrazone hydrochloride with 3,5 dichloro-2-hydroxy-benzene sulfonic acid.

5. The reagent test strip of claim 2 wherein said testing reagent is:

4-aminoantipyrene with 5-oxo-1 (p-sulfophenyl)-2-pryrazoline-3-carboxylic acid.

6. The reagent test strip of claim 1 wherein said testing reagent is:

4-aminoantipyrene with N-(m-tolyl)-diethanolamine.

7. The reagent test strip of claim 2 wherein said testing reagent is:

2,2'-azino-di(3-ethylenebenzthiazoline) sulfonic acid.

8. The reagent test strip of claim 2 wherein said matrix has a thickness of between 100 microns and 3000 microns and a porosity of between 0.5 microns and 150 microns.

9. The reagent test strip of claim 8 further comprising a porous disc on one side of said strip wherein an unmeasured blood sample may be placed on said porous disc such that said sample passes through said disc and a portion of said disc comes into contact with said matrix, and further wherein the side of said strip opposite said porous disc is visible.

10. A reagent test strip comprising:

a uniform porous matrix capable of absorbing a whole blood sample;

said matrix being selected from the group consisting of polyvinyl sulfonic acid, polyethylene glycol, polystyrene sulfonic acid, polyvinyl pyrrolidone, and polyacrylic acid;

said matrix divided into a separating portion and a reaction portion, said separating portion having a separation coating disposed upon an internal surface of the matrix suitable for separating said sample into red blood cells and a substantially clear fluid suspected of containing glucose and said reaction portion of said matrix being capable of reacting with said glucose contained in said substantially clear fluid to vary the coloration of said matrix dependent on the concentration of said analyte in said fluid.

11. The reagent test strip of claim 10 wherein said matrix is selected from the group consisting of:

polyesters, polyamides, polyolefins, and polysulfones.

12. The reagent test strip of claim 10 wherein said reaction portion contains a test reagent present in an amount effective to vary the coloration of said reaction portion comprising 3-methyl-2-benzothiazoline hydrazone hydrochloride with 3,3-dimethylaminobenzoic acid.

13. The reagent test strip of claim 10 wherein said reaction portion contains a test reagent present in an amount effective to vary the coloration of said reaction portion comprising 3-methyl-2-benzothiazoline hydrazone hydrochloride with 3,5 dichloro-2-hydroxy-benzene sulfonic acid.

14. The reagent test strip of claim 10 wherein said reaction portion contains a test reagent present in an amount effective to vary the coloration of said reaction portion comprising 4-aminoantipyrene with 5-oxo-1 (p-sulfophenyl)-2-pyrazoline-3-carboxylic acid.

15. The reagent test strip of claim 10 wherein said reaction portion contains a test reagent present in an amount effective to vary the coloration of said reaction portion comprising 4-aminoantipyrene with N-(m-tolyl)-diethanolamine.

16. The reagent test strip of claim 10 wherein said reaction portion contains a test reagent present in an amount effective to vary the coloration of said reaction portion comprising 2,2-azino-di(3-ethylenebenzthiazoline) sulfonic acid.

17. A reagent test strip comprising:

a matrix having an internal surface and comprised of a polyamide;

said matrix containing a reaction agent comprising 3-methyl-2-benzothiazolinone hydrazone hydrochloride; glucose oxidase; horseradish peroxidase; and 3, 3-dimethylamino-benzoic acid;

said matrix containing a separating coating on said internal surface of said matrix comprising 25% by volume polyvinyl sulfonic acid at pH 4.5 and 1% by weight bentonite;

wherein said matrix is capable of separating whole blood into read blood cells and a substantially clear fluid suspected of containing glucose, said reaction agent reacting with any glucose in said substantially clear fluid to color said matrix, said color intensity varying with the concentration level of glucose in said fluid.

18. A method for testing glucose levels in a porous matrix reagent test strip having a test side and a sample side and defining an internal surface, said matrix having disposed upon said internal surface throughout said matrix both a separation coating and a testing reagent; said method comprising:

placing a sample of whole blood upon the sample side of said strip;

interacting said whole blood with the separating coating and thereby separating said whole blood into red blood cells and substantially clear fluid;

reacting said clear fluid with said testing reagent, said testing reagent causing said clear fluid to vary the coloration of said matrix as a function of the concentration of glucose in said fluid; and observing the change in coloration on said test side.

* * * * *

UNITED STATES PATENT AND TRADEMARK OFFICE
CERTIFICATE OF CORRECTION

PATENT NO. : 5,418,142
DATED : May 23, 1995
INVENTOR(S) : Ernest J. Kiser, Edward G. Rice, and Michael F. Tomasco It is certified that error appears in the above-indentified patent and that said Letters Patent is hereby corrected as shown below:

Col. 9, line 12, change "analyte" to --glucose--;
Col. 9, line 30, change "test" to --sample--;
Col. 11, line 2, change "read" to --red--.

Signed and Sealed this

Twenty-eighth Day of May, 1996

Attest:

BRUCE LEHMAN

*Attesting Officer*      *Commissioner of Patents and Trademarks*